US007984805B2

(12) United States Patent  
Gaba et al.

(10) Patent No.: US 7,984,805 B2
(45) Date of Patent: Jul. 26, 2011

(54) MEDICAL SHARPS RETARDATION APPARATUS AND A METHOD OF RETARDING MEDICAL SHARPS FROM FUTURE USE

(75) Inventors: Rodolfo Gaba, Simi Valley, CA (US); Michael D Griffin, Agua Dulce, CA (US)

(73) Assignee: Griff Industries Inc, Northridge, CA (US)

( * ) Notice: Subject to any disclaimer, the term of this patent is extended or adjusted under 35 U.S.C. 154(b) by 1471 days.

(21) Appl. No.: 11/162,186

(22) Filed: Aug. 31, 2005

(65) Prior Publication Data

US 2008/0021387 A1   Jan. 24, 2008

(51) Int. Cl.
*B65D 83/10*   (2006.01)
(52) U.S. Cl. .......................................... 206/366; 206/365
(58) Field of Classification Search .......... 206/364–366, 206/354, 355, 359; 604/2, 110, 187, 192, 604/263
See application file for complete search history.

(56) References Cited

U.S. PATENT DOCUMENTS

| | | | | |
|---|---|---|---|---|
| 2,953,243 A | * | 9/1960 | Roehr | 206/216 |
| 3,200,486 A | * | 8/1965 | Shields | 29/422 |
| 3,785,233 A | * | 1/1974 | Robinson | 83/167 |
| 4,275,628 A | * | 6/1981 | Greenhouse | 83/167 |
| 4,375,849 A | * | 3/1983 | Hanifl | 206/366 |
| 4,725,267 A | | 2/1988 | Vaillancourt | 604/192 |
| 4,900,500 A | | 2/1990 | Honeycutt | 264/263 |
| 4,927,018 A | | 5/1990 | Yang et al. | 206/365 |
| 4,952,207 A | | 8/1990 | Lemieux | 604/164 |
| 4,956,907 A | * | 9/1990 | Bruno | 29/426.5 |
| 4,961,541 A | * | 10/1990 | Hashimoto | 241/65 |
| 4,986,811 A | * | 1/1991 | Thead et al. | 604/110 |
| 5,183,468 A | | 2/1993 | McLess | 604/164 |
| 5,188,598 A | * | 2/1993 | Thead et al. | 604/110 |
| 5,322,165 A | | 6/1994 | Melker et al. | 206/366 |
| 5,328,482 A | | 7/1994 | Sircom et al. | 604/164 |
| 5,351,381 A | * | 10/1994 | Case | 29/283.5 |
| 5,395,338 A | | 3/1995 | Gaba | 604/110 |
| 5,417,659 A | | 5/1995 | Gaba | 604/110 |
| 5,511,657 A | * | 4/1996 | Gnau et al. | 206/204 |
| 5,558,649 A | | 9/1996 | Shields | 604/192 |
| 5,601,532 A | * | 2/1997 | Gaba | 604/110 |
| 5,662,610 A | * | 9/1997 | Sircom | 604/110 |

(Continued)

*Primary Examiner* — Mickey Yu
*Assistant Examiner* — Jenine M Pagan
(74) *Attorney, Agent, or Firm* — Law Office of Ken Dallara; Ken Dallara (57) ABSTRACT

A medical apparatus whose purpose it is to permanently retard future use of a medical apparatus, in particular needles, preventing accidental exposure to contaminated sharps. It facilitates the possible removal of medical devices from their respective holders, while preventing possible contaminated discharge of fluids located along the anterior or exterior walls of needles or exterior of medical sharps. This medical apparatus provides for single handed use which complies with OSHA guidelines, and its advanced design facilitates the more common shorter medical needles to which non-medical users are accustomed as well as the wide range of needles that medical professional use. This apparatus is easier to manufacture, shorter in stature that allows for its inclusion in the already overcrowded medical trays used by today's medical personnel, in particular, emergency medical technicians. An embodiment contains multiple apparatuses together allowing for safe storage of several sharps, which is a common need in emergency situations both in the field and in the hospital settings, where doctors or technicians are attempting to stabilize critical patients with multiple injections. The apparatus uses counter-opposing gripping devices with an enveloping containment member which serves both to tension the juxtapositionally aligned gripping devices and to prevent leakage of contaminated fluids from medical devices.

22 Claims, 8 Drawing Sheets

U.S. PATENT DOCUMENTS

| | | | |
|---|---|---|---|
| 5,761,975 A * | 6/1998 | Waluda | 82/58 |
| 6,036,671 A | 3/2000 | Frey | 604/110 |
| 6,123,193 A * | 9/2000 | Vojtasek et al. | 206/366 |
| 6,158,314 A * | 12/2000 | Thead et al. | 83/23 |
| 6,319,232 B1 | 11/2001 | Kashmer | 604/192 |
| 6,332,534 B1 | 12/2001 | Hammett | 206/366 |
| 6,413,243 B1 | 7/2002 | Geist | 604/192 |
| 6,511,461 B2 | 1/2003 | Jonsson | 604/240 |
| 6,545,242 B1 | 4/2003 | Butler | 219/68 |
| 6,592,556 B1 | 7/2003 | Thorne | 604/192 |
| 6,595,955 B2 | 7/2003 | Ferguson et al. | 604/110 |
| 6,632,201 B1 | 10/2003 | Mathias et al. | 604/263 |
| 6,649,857 B1 * | 11/2003 | Guerra | 219/68 |
| 6,695,819 B2 | 2/2004 | Kobayashi | 604/192 |
| 2002/0123721 A1 * | 9/2002 | Payne et al. | 604/110 |

* cited by examiner

MEDICAL SHARPS RETARDATION APPARATUS AND A METHOD OF RETARDING MEDICAL SHARPS FROM FUTURE USE

BACKGROUND OF INVENTION

Since the knowledge that blood borne pathogens and diseases can be passed from the carrier to another being, science has been concerned about the possibility of accidental needle puncture by unshielded sharp needles. Recently with the advent of the spread of AIDS and Hepatitis strains through blood contact, there has been added emphasis on the need to prevent accidental needle puncture by those using the needles or by those whose task it is to dispose of used needles. Also there exist a need to prevent secondary use of hypodermic style needles by those outside of the medicinal users, such as intravenous drug abusers, in the prevention to reduce the spread of these diseases that are spread by contact with contaminated blood. As technology has improved, so has the ability for needle manufacturer to develop sharper needles with smaller bores, increasing the chance of accidental puncture by these smaller sharper needles. Technology has also increased the safety of certain medications, in particular insulin to allow for non-medical personnel to administer or in some cases, self administer, injections of these medications. These non-medical users do not have the level of experience of medical personnel in the use of sharps containment, nor in many cases, do they have the financial means to use expensive injection devices that integrally contain sharp needle containment devices. Typically, these users are using non-refillable or single use injection devices. Unfortunately recently, used single-use hypodermic needles that have not been properly covered and disposed of, have found their way into city streets and have washed up on public beaches.

OSHA in it's 1991 Blood Borne Pathogens Standard, codified under 29 CFR 1930.1030, has noted that re-capping or containment of contaminated needles must be done through the use of a mechanical device or a one-handed technique, immediately or as soon as possible after use. These containment devices serve two purposes; one is to prevent accidental needle puncture, and secondly to contain or encapsulate any blood, and thus blood borne diseases, from being able to discharge from the needle into non-contaminated areas where human contact is possible. Thus, there exists a need for an inexpensive, easy to use, compact and reliable sharps containment device that will cover the sharp needle and prevent evacuation of contaminated fluids, after use and throughout the disposal process, after being used by either experienced medical or non-medical personnel. This invention defines a method of designing a device which can permanently hold a medical sharps, such as needles or trocars, in such a device that permanently retards their ability to be re-used.

Currently available sharps containment devices that protect the sharp tip of the needle can be broken down into three classes; those that cover the entire needle, those that slide down and protect only the tip of the needle, and those that where the user inserts the needle into a device. In the class of protectors that cover the entire needle after use, there is either an external sheath that is not integral to the hypodermic needle syringe body or an object that flips down on a pivot to cover the used needle. This sheath is either positioned along with the entire syringe body, as U.S. Pat. No. 5,558,649 issued to Shields on Sep. 24, 1996 and U.S. Pat. No. 5,851,196 issued to Arnett on Dec. 22, 1998 disclose, or is placed onto the needle hub, as U.S. Pat. No. 4,725,267 issued to Vaillancourt on Feb. 16, 1988, and U.S. Pat. No. 4,887,998 issued to Martin et al on Dec. 19, 1989 disclose. These are attached after the initial manufacture of the syringe body increasing cost and complexity of the process. Attaching these devices to the syringe body or needle hub increases the chance of chipping or damaging the end of the fragile needle, causing a burr, which causes the patient much unneeded pain. Also the devices are attached when the needle is exposed, increasing the risk of accidental needle puncture, the very act that is trying to be eliminated. There are also issues regarding the sterilization of these attached devices. Once the sterile package is opened to install these shields, the syringe must be immediately used or must be re-sterilized. This added step complicates activities in medical situations where extra steps could lead to time better spent saving patients, especially in settings outside of the hospital. The action to cover the needle, once the sheath is retracted for use, with these devices is to activate the returning of the sheath to the cover position by slight mechanical force. Accidental discharge of the devices holding the needle sheath in the retracted or use position, will render the syringe device completely unusable. Another drawback from using this style is the inability of the device to completely encapsulate the needle tip to prevent leakage of contaminated fluids. There must an opening that allows the sheath to be in a retracted position over the needle. Some of these sheathes also use unique or proprietary syringe bodies where special ribbing or holding devices that have been attached to facilitate the addition of the sliding cover. This adds greatly to the cost of the devices and adds many unique parts to hospital inventories, who are trying to reduce their inventory carrying costs. Prior art of this style is typified by U.S. Pat. No. 4,927,018 issued to Yang on May 22, 1990. Such special needles are expensive and do not integrate with current medical practices that seek to use devices that are accepted as standards in the industry. Other styles are designed solely for catheters, such as U.S. Pat. No. 5,769,827 issued to DeMichele et al. on Jun. 23, 1998, where it uses a special needle along with a proprietary syringe body. These aforementioned prior arts are constructed so that the needle hub is completely covered by the device prohibiting the removal of the needle from the syringe body. Other styles are designed for specific medical practices or procedures, such as U.S. Pat. No. 6,478,780 issued to Shields on Nov. 12, 2002, where this expensive and complex device is designed for only dental or plastic surgery applications.

The flip down style is also attached to the needle hub as a secondary operation to the manufacture of the syringe. Some are installed onto an open, unprotected needle prior to use. U.S. Pat. No. 4,664,259 to Landis issued on May 12, 1987, and U.S. Pat. No. 6,319,232 to Kashmer on Nov. 20, 2001 disclose a package that is attached to the needle hub. As before, to attach this device to the needle hub requires the needle be exposed, allowing the possibility of needle chipping, or needle puncture. Also due to the need to have clearance to open the device to use the needle, there are openings where contaminated blood or other bodily fluids can escape from the needle and possibly infect others. U.S. Pat. No. 6,413,243 to Geist issued on Jul. 2, 2002 does not have the problem of openings where blood can escape or having to expose the needle to attach the device, but presents an overly complex device, with latching members and interlocking engaging members, that require two-handed operation of this device. It also is very expensive for the average user and also presents a bulky operation not suited to emergency activities or to the single user without assistance of other medical personnel. U.S. Pat. No. 6,592,556 to Thorne issued on Jul. 15, 2003 eliminates the abovementioned problem of attachment to an unprotected needle and two handed operation, but does not completely encase the needle allowing for contaminated fluid discharge, as well as being an expensive attachment for the average user. U.S. Pat. No. 6,695,819 to Kobayashi issued on Feb. 24, 2004 combines a flip down needle protector that integrates with a needle cover. This device also is attached onto an unprotected needle and uses a proprietary needle cover and the flip down device does not cover the entire needle allowing for contamination. This device, by it design, does not allow for one-handed operation, which is critical to OSHA guidelines and emergency use, where emergency personnel are often performing multiple tasks at a single moment, such as holding down an IV tube into which the contents of the syringe will be emptied. Single handed operation of the needle protection device is a must in these situations.

In the arena of those devices that slide down and protect only the tip of the needle, U.S. Pat. No. 6,595,955 to Ferguson et al, issued on Jul. 22, 2003, discloses use of the device on a hypodermic needle, that must first be slid down the needle bore in order to be in the correct location for use after the syringe has been used. There are four inherent problems with this approach, as the needle is exposed during the task of installing the device, subjecting the user to accidental puncture; the device is too big to fit on today's small shorter hypodermic needle; the addition of this device to the needle creates an obstruction to the user in positioning the needle in the optimal striking angle into the skin or the user must be cognizant of the position of the device when using the needle, an additional item with which to be concerned in emergency situations; the device requires two handed operation to properly and safely use the device. Other prior art includes the use of such devices on much larger catheter style needles. U.S. Pat. No. 5,183,468 to McLess, issued on Feb. 2, 1993, discloses the fact that the device that is placed on the hub of the needle prior to use requires the use of a longer needle and also discloses that smaller devices of this style require close tolerances and miniaturized components, that both greatly increase the cost of the device to the user. U.S. Pat. No. 4,952,207 to Lemieux issued on Aug. 28, 1990, discloses a device that requires a special needle with a slot cut into the tip section for the device to attach onto for a secure fit. These special needles are expensive and do not fit into the need for standardizing needles and syringes throughout the medical community. U.S. Pat. No. 5,533,974 to Gaba issued on Jul. 9, 1996 discloses a spring powered latching device that is complex to manufacture and is to suitable for the smaller hypodermic needles.

Finally, those devices that are designed so that the user inserts the needle into the device which prevents withdrawal of the needle therefrom are examined. The current invention falls into this category. This methods avoids the problems with the aforementioned prior art, whereby the user does not prematurely subject themselves to the chance of accidental puncture or damage of the needle by having to install in the device onto the needle, allows for single handed operation, completely seals the needle from escape of contaminated fluids and is not a hindrance to use as the device is not in the line of sight or use, by merely being located on the needle itself. There are two main methods of preventing the user from withdrawing the needle from the device, once it is inserted; Either Chemical or Mechanical. In the chemical arena, the devices either capture the needle in a chemical compound that hardens to prevent removal, such as U.S. Pat. No. 5,322,165 to Melker issued on Jun. 21, 1994 using two part resin, U.S. Pat. No. 4,900,500 to Honeycutt issued on Feb. 13, 1990 using oligomer or monomer composition, U.S. Pat. No. 4,845,923 to Donovon issued on Jul. 11, 1989 using polyurethane foam, U.S. Pat. No. 5,368,576 to Brown et al, issued on Nov. 29, 1994 using a curable adhesive or U.S. Pat. No. 6,332,534 to Hammett issued on Dec. 25, 2001 using an epoxy resin. The problem with chemical hardening is the time it takes to secure the needle into the mixture as the mixture hardens around the needle as well as the problem associated with how fragile the unit is to accidental contamination of the agents causing premature hardening. The devices are not suited for emergency situations where speed is critical to success. Other devices are large table mounted units, not suitable for field applications, such as U.S. Pat. No. 6,545,242 to Butler issued on Apr. 8, 2003, which actually melts the needle destroying the needle from further use and also any associated contamination on the needle. In the mechanical arena, a syringe with the needle attached is placed into a device which holds it securely, retarding it's further use. U.S. Pat. No. 6,511,461 to Jonsson issued Jan. 28, 2003 discloses a device which is designed for needles performing extracorporeal blood processing where the needle is only held through friction between the needle and a deformable disk, which is not a sufficient amount of retardation as the patent discloses the possibility of dislodging the syringe needle from the device in the presence of force. Any possibility of dislodgment is not acceptable when persons outside of the medical needs situation, can recover needles and use the syringe and needle for illicit use. U.S. Pat. No. 5,395,338, which is a continuation of U.S. Pat. No. 5,417,659 to Gaba issued on Mar. 7, 1995 and May 23, 1995 respectively, disclose prior art most closely associated with the present invention. Gaba claims a foil which uses a wedging element along with a biasing element and a gripping element to create a binding force to hold the needle in position inside of the foil. This combination creates four principle problems. Firstly, the combination of the 3 elements creates a stack of elements that are too tall for the newer shorter units and as Gaba claims a stop for limiting needle insertion, the shorter needles will not be gripped by the gripping element. By design, there will always be an extra element that the current invention does not possess, the wedging element. The preclusion of that element creates the shorter stack height that is necessary. Secondly, the wedging elements are difficult to assemble properly, causing slow production cycles or quality failures. The direction of the bias or discontinuity on the gripping element must face away from the opening of the device, and the operator is forced to examine each gripping element for the direction of the bias. Trying to find the bias of the wheel is difficult as the bias is in the same color as the wheel and the bias is less than 0.0005 in height. This lack of definition makes cheaper more automated forms of assembly, such as robotic assembly, very difficult and expensive as extensive vision systems are required. Failure to orientate the bias properly will lead to failure of the device as the needle will slip against the gripping element. These quality failures are not discoverable once the unit is sealed until the foil is used. Improper assembly causes the gripping element not to grab the needle with sufficient force to hold the needle in place. Thirdly, Gaba discloses the necessity for the discontinuity of the gripping element to be sharp. Gaba claims that the discontinuity will distort the sharp in claim 3 of Gaba '659, so that there is a mechanical interference so that the wedging element performs properly. With advances to needle technology where stronger needles are being sought and designed, there is no method to assure that future needles are distortable by the Gaba device. Also, other medical sharps like blades, disclosed by Gaba, constitute a class of medical sharps that by their nature deter the ability to distort their shapes as this quality would be detrimental to their medical performance raising doubts as the adequate performance of the Gaba device. The current invention uses the principle of mechanical leverage not friction to prevent the retracting of medical sharps which precludes the need to mechanically distort the medical sharp. Leverage is defined as a force transmitted through a pivoted point by an object. The mechanical leverage comes about as the gripping means are forcibly rotated about the pivot point. As the sharp is attempting to be withdraw from the invention, the gripping means are forced or leveraged against one other, as the pivot point is not along the centerline of the gripping means, thereby trapping the sharp between the gripping means. Fourthly, current adaptation of the Gaba patent has a cover that slips onto the device, whose purpose is to engage the hub of the needle and allow the user to rotateably remove the needle from the syringe body. This cover can be relocated from its position on the device, along the shaft of a needle, so that once the needle is inserted into the Gaba device, the user can slide the cover up to the hub of the needle and rotate the syringe body until the needle is separated from the syringe body. This cover has two inherent problems. Firstly, the cover adds to the height of the stack, further precluding the use of short needles as the height of the stack is increased by about 25%. Secondly, the cover must be attached prior to use of the device. If the user decides after the fact to remove the needle from the syringe body, the user is not able to use the cover for that operation.

It would be desirable to have a apparatus that is able to work with needles of all different medical, dental, veterinary types of needles, devoid of the problems associated with the prior art, and is able to provide this protection in a cost-effective manner. Another embodiment of the present invention is that it also functions separately as a apparatus to hold needles so that they can be removed from the syringe bodies. A separate wrench that is attachable even after the needle is inserted into the apparatus is adapted for use. This wrench can also be detached from the apparatus after the needle has been removed from the syringe body, and the wrench can be reused on another apparatus. This reusability is a desirable function.

The current invention also includes a multiple apparatus arrangement whereby more than 1 apparatus is available for use at any one time. During surgery, many needles are used in rapid succession causing the need for one unit to adapt to many needles quickly. It would be desirable to have an apparatus that is small enough to fit into the crowded surgical trays used in today's operating room, and yet be stable enough to resist tipping.

SUMMARY OF INVENTION

It is the primary object of this invention to disclose an improved needle retarding apparatus, especially one which involves the apparatus described hereinafter, wherein this new invention creates a apparatus which is cheaper, more secure, with greater gripping strength and is more easily assembled then is currently available. It is a further object of this invention to create a apparatus for this purpose that is easier to use for both the medical professional and the common layman, both of whom are forced to deal with the smaller, shorter single use needles. It is desirable that this invention creates an apparatus which is not associated with any of the problems that are aforementioned in detail, such as having to install the apparatus onto an exposed needle or having the possibility of contaminated fluids escaping from the sharps device into an area where it might contaminate others. It is a further object of this invention to create a apparatus that will conform to OSHA guidelines of single handed use and permanent retardation from future use of single use needles. It is a further object of this apparatus to be designed so that the individual pieces that make up the unit can be injection molded using thermoplastic materials. It is a further object of this apparatus to double the gripping strength by having two entities gripping the needle rather than only one entity as in the prior art. It is a further object of this invention is to design such a apparatus that can be produced as a single version or a apparatus with multiple entry points for multiple needles to use as in the field as in the operating room, multiple needles are often used in quick succession requiring many sharps to protect quickly.

In accordance with the objects of this invention, a simplified apparatus is created that contains an encasement, gripping means, needle hub removal means, and an enveloping containment member. The user simply inserts the used medical sharp after use into the opening of the housing and the sharp is permanently retarded from further use as a medical sharp. The user performs this operation single-handedly and the user is not subjected to accidental puncture by installing this apparatus prior to use.

The apparatus, as previously mentioned, though singular in nature, is capable of multiple configuration, including but not limited to sets of 2 or 4 entry points in a single enclosed encasement. Though only disclosing single and a 4 entry point apparatus, there is no limit to the variations available and are thus part of the spirit and scope of this invention. Though this apparatus is disclosed as having a circular encasement, polygonal encasements are possible and as such are part of the spirit and scope of this invention.

The housing of the apparatus consists of an open end and a closed end. The housing consists of two pieces that forms one encasement, one piece which is the upper body and the second piece is the lower lid. The upper housing contains pivot means upon which the gripping means rotate thereupon, eliminating the need for a separate wedging element that is found in the prior art and forming a fulcrum of mechanical leverage. The encasement is constructed of such material that the material is capable of being conjoined together to create a hermetic seal, while being strong enough to prevent the medical sharp from protruding from the lower lid when the medical sharp in inserted to the apparatus with significant physical force. In the preferred embodiment, the material is a polymer such as ABS. The encasement also contains the gripping means and the enveloping containment member which are assembled into the upper housing. The gripping means consists of circular members which has embossed upon it a pattern of cross-hatching or angular grooves that are sufficient in depth and width to hold the sharp that is placed into the encasement. In the preferred embodiment, the gripping means are constructed of two round stainless steel wheels with flat sides with a circular perimeter with a knurling pattern approximately 0.0005 of an inch deep applied prior to heat-treatment of the wheels. Another gripping means that can be used are spherical stainless steel objects with a similar knurl applied. The term knurling will be understood by those having knowledge in the art, as a means for changing the surface texture of an object by the addition of series of small ridges or beads to create small protuberances increasing the surface area of the object. The direction of the bias on the gripping means is not critical as the multiple gripping means act in unison to create the leverage necessary to prevent the sharp from being removed from the apparatus. This invention eliminates the number of pieces that must be carefully inserted. Prior art is too detail oriented to allow for fast or automated assembly. The current invention eliminates the need for detailed orientation of the pieces, allowing for faster or automated assembly.

The enveloping containment member is constructed of a polymer which is soft enough to accept the injection of the sharp thereinto, yet is firm enough to hold the gripping means in location prior to the insertion of the sharp into the apparatus. The enveloping containment member must be of such material that it envelopes that portion of the medical sharp injected thereinto, and such that there is created a seal whereby any fluids contained thereon or therein the medical sharp is prevented from escaping from the encasement. In the preferred embodiment, a polyvinylchloride, with a Shore A hardness between 45-70 preferably 54, material is used. The enveloping containment member is specially shaped with circular protrusions that hold the gripping means in place against the interior of the upper body. The protrusions must be designed as such to allow the gripping means to relocate laterally upon the insertion of the medical sharp, but not to the extent, as to prevent the gripping means from not tangentially contacting the medical sharp at all times. The circular design of this enveloping member is another improvement over the prior art. The prior art has an enveloping member that must be strategically placed into the housing so that the single gripping means will function properly. This detailed placement makes for a less efficient and productive construction of the prior art devices, and makes automation of the assembly of the prior art device more costly, if at all. The current invention's enveloping member is not locationally unique, so any orientation of the enveloping member by human assemblers or an automated device is simply performed. This enveloping containment member is shaped in such a manner as to allow both the protrusions and the target area to be shaped in such a manner to allow the medical sharp to be enveloped by the target area following the medical sharps contour as well as providing space for the protrusions to engage the gripping means. An embodiment of this invention is a wrench that has a gripping slot which integrates with current needle hub and syringe designs, whereby the gripping slot adepts into the ribs of the needle hub, securing a fit that enables the user to hold the cover and rotate the syringe body and remove the needle and the needle hub from the syringe body. Future designs of the wrench will facilitate upgrades in hub designs.

Anyone who is knowledgeable in the art, will realize that the shape of the apparatus as well as the opening through which the medical sharp will enter the apparatus, will correspond to the contours of the medical sharp, and that this invention is not limited by the type of medical sharp. This invention shows the techniques and methods of capturing and holding the medical sharps. The configuration of the encasement will naturally follow the shape and size of the medical sharp. A needle is used here as an example, but does not limit this application to only needles as medical sharps. Anyone knowledgeable in the field will recognize that the term medical sharps refers to any instrumentality that contains a portion whose purpose is to puncture or cut subcutaneously.

DETAILED DESCRIPTION

Figure 1:
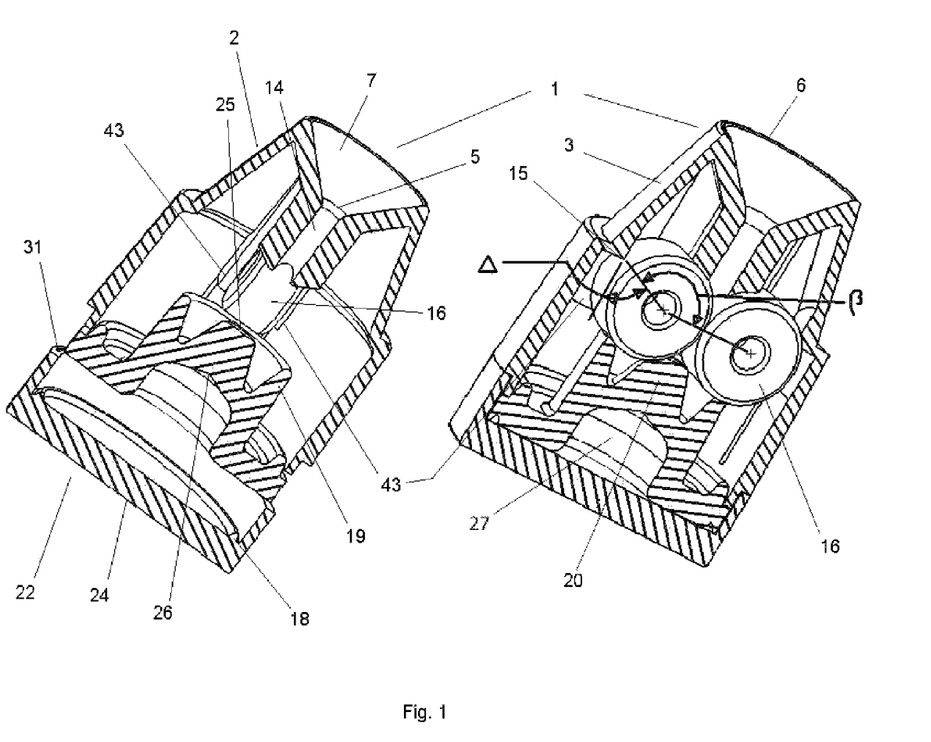
In FIG. 1, the cross-sectional view of the single unit apparatus is shown.
Figure 2:
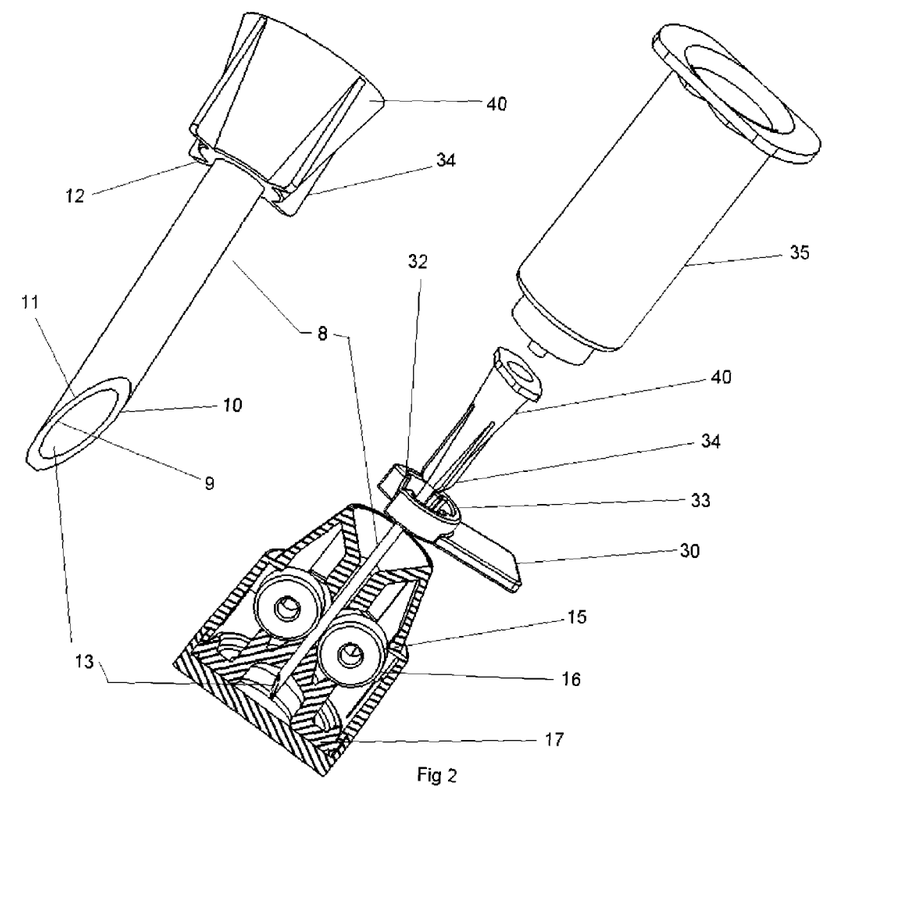
In FIG. 2, a cross-sectional top view of the apparatus showing a view of needle in the apparatus and a close-up view of needle, the syringe and the unwinding wrench.
Figure 3:
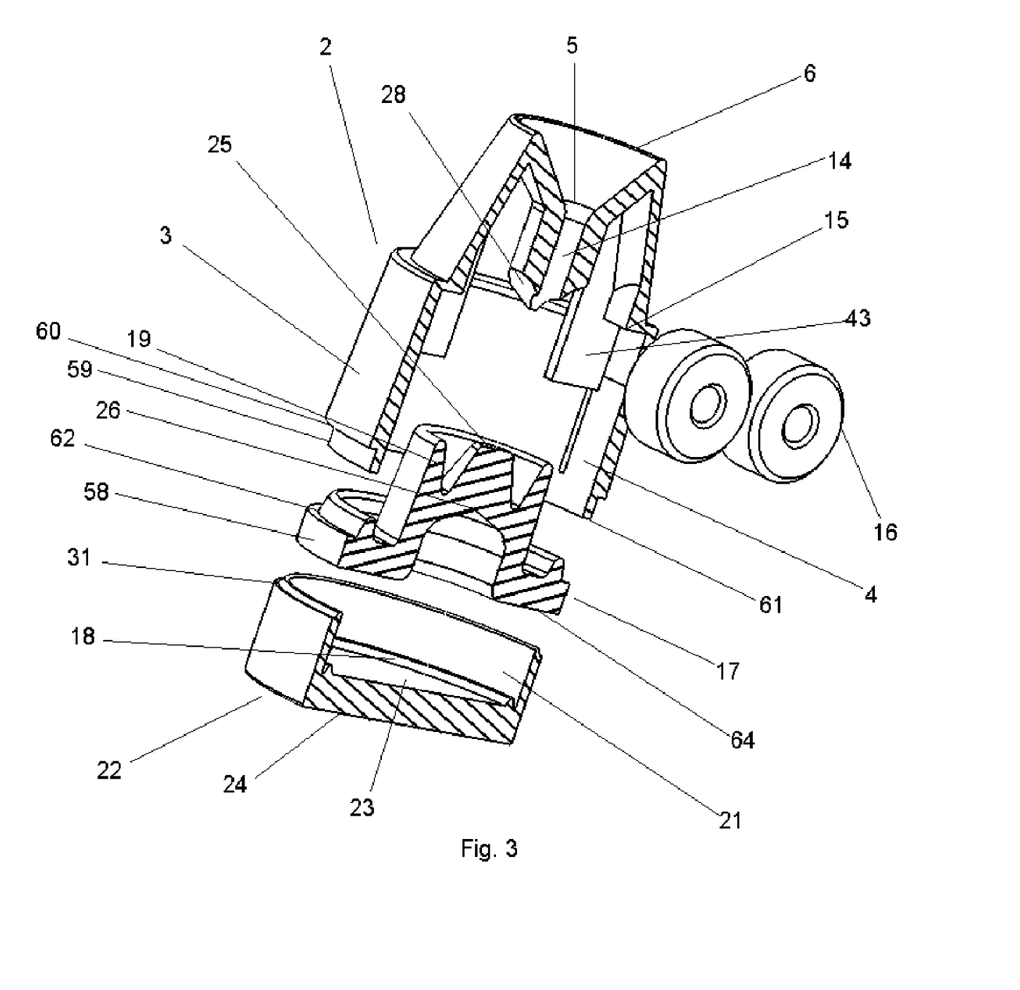
In FIG. 3, the assembly of the single unit apparatus is shown in an exploded view.
Figure 4:
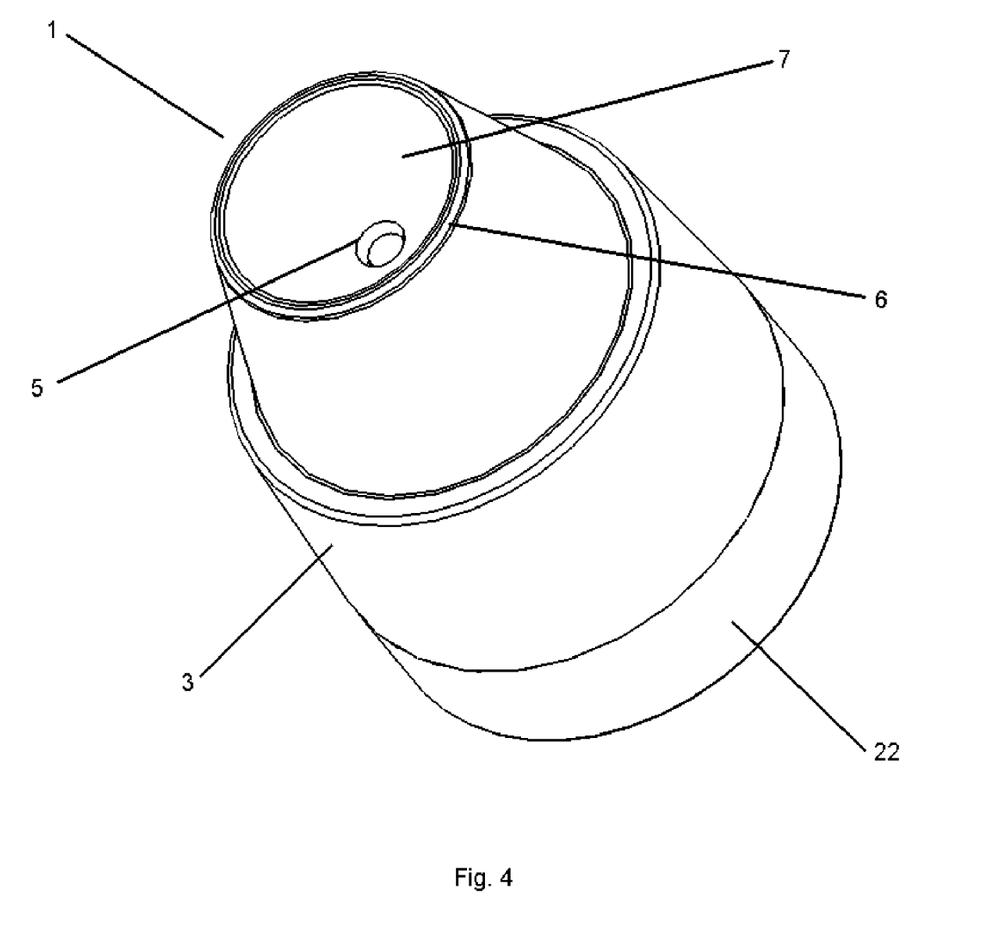
In FIG. 4, the single unit apparatus is shown assembled in a top view.

In FIG. 1, the encasement of apparatus 1 is shown in cross-sectional views. In FIGS. 2 and 3, the details of the invention are shown exploded and in use. Upper housing 2, contains an exterior portion 3, along with an interior portion 4 with sharps entrance opening 5 that is located subjacent to targeting ring 6. Interior portion 4 symmetrical about the centerline of the apparatus. Both upper housing 2 and bottom encasement lid 22 are designed such that they are able to be injection molded using thermoplastics. Sharps entrance 5 is located on the closed end of upper housing unit 2 which is opposite to open end of upper housing unit 2. Bottom lid 22 has an interior surface 23 and an exterior surface 24. FIG. 4 shows the locating means shown here as targeting ring 6 that is connected to sharps entrance open 5 by centering slope 7, which is angled in an acute manner that serves as a positioning of the medical sharp into the proper orientation for insertion through sharps entrance opening 5. In this instance, the medical sharp is a needle 8, and thus the sharps entrance opening 5 is circular in nature, corresponding to the circular nature of the medical sharp. Sharps entrance opening 5 can be modified in such a corresponding manner as to accept whatever medical sharp is needing to be placed into the apparatus. In this instance, a needle such as a hypodermic syringe needle, is shown in FIG. 2. Needle 8, has an interior wall 9 and an exterior wall 10, and has an open end 11 which is opposite of enclosed end 12. Enclosed end 12 is located inside of a needle hub, 40. Open end 11 is angled with an acute angle which creates a circumscribed opening 13, through which medication or blood passes through during the use of the needle. Needle 8 passes beyond sharps entrance opening 5 into interior passageway 14 which is located in the circumferential center of the upper housing 2. Interior passageway 14 is located on the center of gravity of the encasement 1 so that there exists a lower chance of the encasement 1 tipping over during use. There exist a pivoting means that allows gripping means 16 to rotate thereabout. In this example, there exists at least two pivot points 15, which are located equidistant from the vertical centerline of the upper housing 2 to a location along the interior portion 4. In this invention, the pivoting means are sharp corners created by walls in the interior portion 4, but is not limited to this design. Any use of an object that permits uninhibited motions about itself is considered a pivoting means. The purpose of the pivoting means is to create the fulcrum point necessary for mechanical leverage to be created. These pivot points 15 allow the gripping means 16 to pivot through a point where the gripping means 16 can rotate to a position that allows the needle 8 to be inserted through interior passageway 14 and into the enveloping containment member 17 without undue force. The distance from the centerline of upper housing 2, which is located through sharps entrance 5 and the point of circumferential contact between the gripping means 16, to the pivot point 15 is angularly measured from the point of contact of the gripping means to pivot point 15 through the centerline of the gripping means 16. This angle, beta, is between 140 to 180 degrees, preferably 150 degrees, is dependent upon the radius of gripping means 16. The angle of rotation of through the center of said gripping means 16 about the pivot point 15 is angle Delta, which is between 40 to 75 degrees, preferably 60 degrees at rest or prior to use position. Angle Delta reduces up to zero depending on the width of said needle 8. The interior design dimensions are only critical to maintain the gripping means 16 in tangential contact with one another in the natural state prior to apparatus usage. The gripping means 16 contact is maintained in the natural state by an upward force directed toward the sharps entrance opening 5, which is created by the buoy arms 19. As gripping means 16 are upwardly forced, gripping means 16 are held in the vertical plane by pivot point 15, gripping element alignment means 28, and contour wall 28. In this invention, contour wall 28, in contact with the upper quadrant of gripping means 16, has a radius that is similar to radius of gripping means 16 and are located symmetrically about interior passageway 14, positioned such that gripping means 16 are held in tangential contact with each other. The gripping means 16 rotate outwardly, away from the centerline, about the pivot point 15 during use. The displacement of the gripping means 16 is limited by the rotation angle Delta created as the gripping means 16 rotates upon the pivot point 15 as gripping means 16 are kept in their location in the lateral or horizontal plane by gripping element alignment means 43. Gripping means 16 are loosely placed between gripping element alignment means 43. Gripping element alignment means 43 are only used to keep the gripping means within the centerline of sharps opening 5. In this example, gripping element alignment means are shaped as solid walls, but this does not limit the function of the means to only solid walls. When needle 8 is inserted through interior passageway 14, gripping means 16 are forced apart as they rotate upon pivot point 15 away from contour wall 28. Gripping means 16 rotate upon pivot point 15 maintaining tangential contact with needle 8 at all times. Enveloping containment member 17 has an exterior side 25 into which the medical sharp is inserted therein, and an interior side 26 which may be a conical dome in shape. During needle 8 insertion, and until the needle 8 has developed contact with the interior surface of bottom lid 23, where needle 8 has pierced enveloping containment member 17 through hollow hub 20, the gripping means 16 have been buoyed by buoy arm 19 that is integral to enveloping containment member 17. The buoy arm 19 and hollow hub 20 is located such that they tangentially touch the gripping means 16, and in such a manner that the gripping means 16 are held in osculation with each other, aided by solid walls of the gripping element alignment means 43. The buoy arm serves to provide resistance while the gripping means 16 rotate about pivot point 15, but also causes gripping means 16 to maintain contact with needle 8 during and after the insertion process by resisting the retraction of the gripping means 16 away from needle 8 by providing upward force to said gripping means 16. The enveloping containment member 17 has hollow hub 20 integral thereto, which serves to envelop the medical sharp, in this case needle 8, and prevent the escapement of contaminated fluids that may be present in either the interior wall 9 or the exterior wall 10 of needle 8, out of the encasement 1.

It is a feature of this apparatus to positively prevent escapement of fluids from the interior or exterior of the sharp once it has been inserted into the apparatus. This positive prevention is performed by 2 functions. There exists a containment sealing means that prevents the escape of fluids from the tip of the sharp once it has pierced the enveloping member and there exist hermetic sealing means that creates a hermetic seal between the upper housing unit and the bottom lid. In this invention, the containment sealing means consists of a series of compressed flexible seals on the enveloping member 17 as it contacts static surfaces of the bottom lid 22 and of compression ring 61. This does not limit the containment sealing means to only this style. Bottom lid 22 has the escapement prevention seal 18 for enveloping containment member 17. Upon assembly of apparatus 1, seal 18 maintains contact with the flange of the lower surface of enveloping containment member 17 so that any fluids that may leak out of needle 8 will be contained inside of the conically shaped dome 26 under the enveloping containment member 17 away from the edges of the bottom lid 22. This is an additional safety measure built into the apparatus. Open end of said upper housing is bordered by containment sealing means in the form of compression ring 61 which provides compression upon upper circumferential ring 62 of enveloping containment member 17 upon completion of the hermetic seal between interior lip 21 and upper housing 2. Compression ring 61 provides positive compressive force which insures positive contact of the lower side 64 of enveloping containment member 17 to seal 18. The circumference of the exterior side of enveloping containment member 58 is such as to maintain contact with proximal end of interior lip 21 of bottom lid 22. Sealing wall 59 of the upper housing 2 creates a hermetic seal when it becomes in contact with the distal end of interior lip 21. This overlapping interference shear fit on interior lip 21 prevents escapement of contaminated fluids that are present in the interior of upper housing unit 2, after the insertion of needle 8 into the apparatus. This is a safety precaution to assure that there is no escaping of fluids out of the apparatus through the bottom of the encasement 1. Interior lip 21 also serves the purpose of centering the enveloping containment member 17 within upper housing 2 during assembly. Hermetic sealing means in this invention involve the use of ultrasonic welding energy directed by the stated design of the plastic parts and the use of thermoplastic materials that will aid in this style of welding. This does not limit the hermetic sealing means to only this style, as there are other forms of attachment of plastic parts to one another that involve a bonding material, whereby the plastics are melted and reformed, sometimes in the presence of pressure. Use of other materials other than plastic are contemplated and the design of the sealing areas would be redesigned as necessitated by the actual material and the bonding method. This invention details the amount of duplicative sealing means that are present to protect the users and those who might come in contact with possibly infected sharps. Distal end of interior lip 21 contains a circumferential hermetic butt-weld bonding seal as weld director 31 which is designed to become molten immediately upon contact with the shoulder welding shear 60, providing additional material with which to aid in the hermetic seal between bottom lid 22 and upper housing unit 2. Weld director 31 shall conform to the acceptable standards for height and width of commonly accepted ultrasonic standards. Any contaminated fluids would have to escape from the seal 18 as well as the hermetic seal between the upper housing 2 and bottom lid 22. This is a remote possibly with the current invention where the Gaba patent only relies on a single seal area to prevent escapement of fluids.

In an embodiment of this invention, a wrench 30 has been invented. Wrench 30 contains needle hub gripping means 32 located on the interior portion of engagement ring 33. Gripping means 32 are configured to match existing common needle hub design, in such a manner as to grip upon the rib of needle hub 34. Needle Hub 34 also encloses needle enclosed end 12. Gripping means 32 engages needle hub 34 with sufficient friction, either through engagement of ribs on needle hub 34 or smooth exterior wall of needle hub 34, to facilitate the rotation of syringe body 35 and subsequent removal of needle hub 34 from syringe body 35. Wrench 30 is designed to allow user to remove wrench 30 from one apparatus and be used on another similar device.

Figure 5:
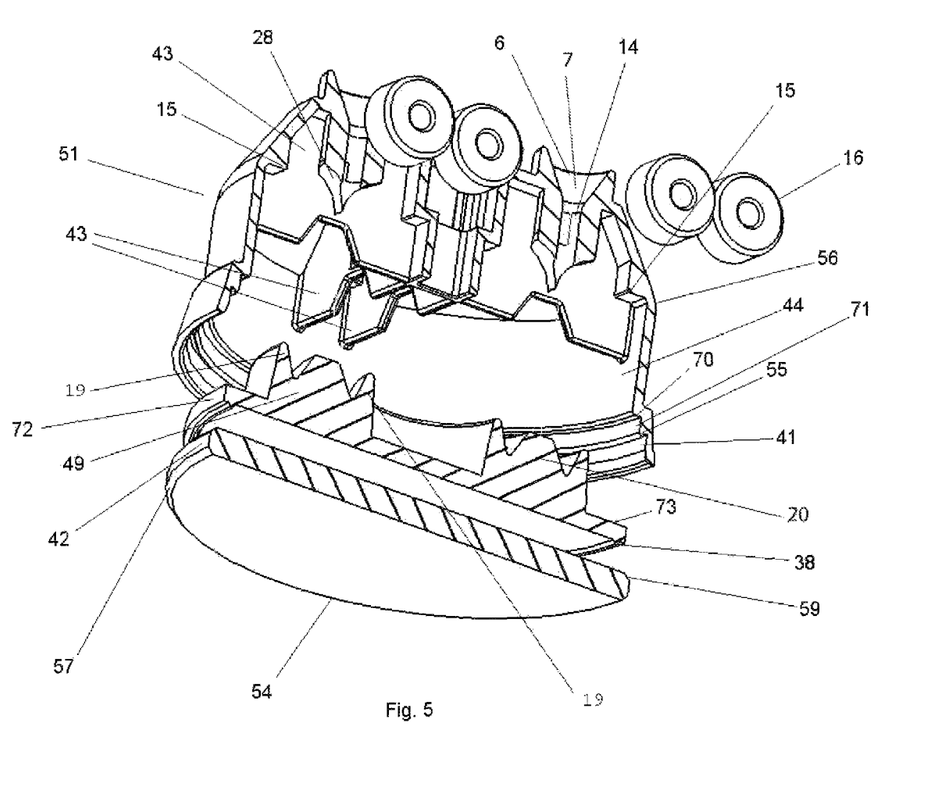
In FIG. 5, an exploded view of a 4 unit apparatus is shown
Figure 6:
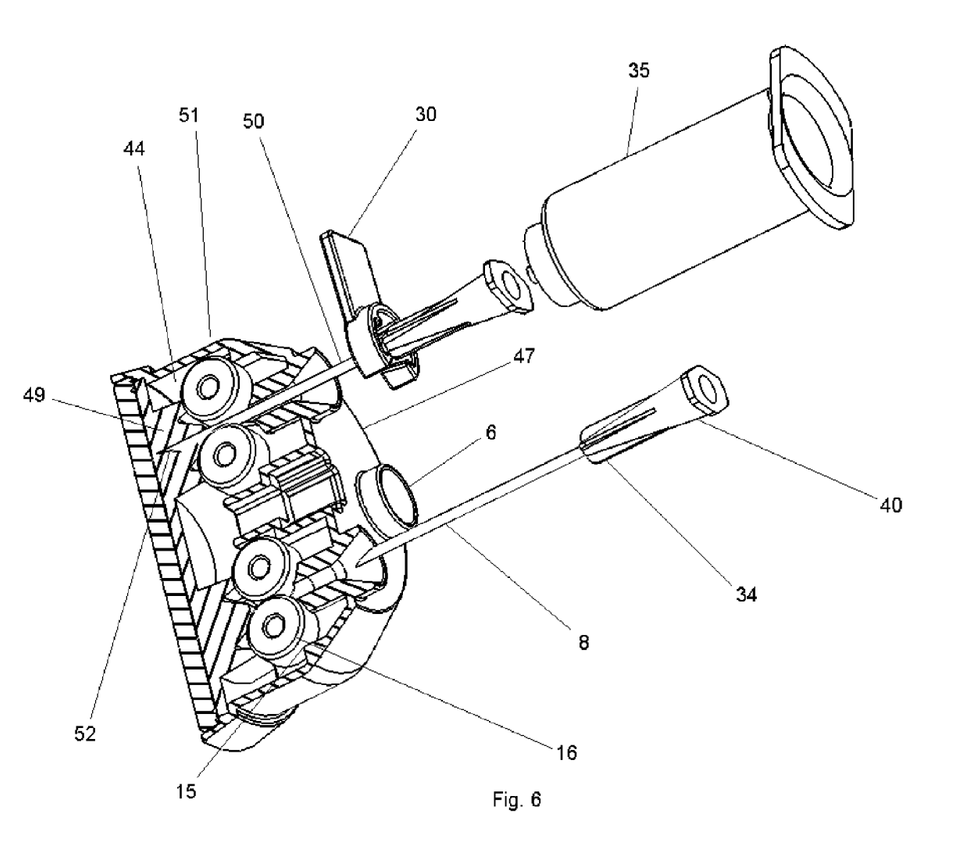
In FIG. 6, the cross-sectional view of the 4 unit apparatus is shown with needles before and after insertion into the apparatus and the unwinding wrench.

FIGS. 5, 6, 7 and 8 show the embodiment of a 4 unit apparatus 51 in a cut away, top and exploded views said apparatus 51. Said 4 unit apparatus 51 is an embodiment of the single needle encasement 1, where 4 needles are able to be placed thereinto through targeting ring 6, guided by centering slope 7 and are able to be permanently retarded from future use. This does not limit the scope of the invention to only single or 4 unit apparatuses, this embodiment is shown to disclose a 4 unit apparatus of the present invention. Multiple unit apparatuses are covered by the spirit and disclosure of this patent. FIG. 6 also shows said gripping means 16 in the two positions prior to and after the insertion of the needle 8 into the apparatus. Needle 50 has been inserted and is permanently retarded from future use. Note the position of the sharp tip 52 deep within the solid enveloping member 49. On the left hand side of the apparatus in FIG. 6, said gripping means 16 have rotated outwardly toward outer wall 44 upon pivot point 15, while maintaining contact with the exterior of needle 50. On the right side of the apparatus in FIG. 6, said gripping means 16 are in tangential contact prior to the insertion of needle 8. Gripping means 16 are held in position between positioning walls 43 and have upward pressure provided by quad buoy arms 39. As in the single unit, contour wall 28 and pivot point 15 provide positive stops in the vertical plane countering the upward forces of buoy arm 19. FIGS. 5 and 6 also details the 5-fold containment safety barriers in this 4 unit apparatus 51. First safety is the complete covering of the sharp tip 52 by the solid hub 53. Solid hub 53 complete encapsulates the sharp tip 52 preventing any leakage of possibly contaminated fluids. Second safety is seal lip 38 which projects downwardly from solid enveloping member 49. Seal lip 38 flattens upon the interior portion of quad bottom 54 during assembly. This creates a positive seal between quad bottom 54 and solid enveloping member 49 preventing the escapement of liquid sharp tip 52 if sharp tip 52 should completely pierce solid 53 hub. Thirdly, FIG. 5 details the location of weld ring 55 on quad upper housing 56. Weld ring 55 flattens upon the quad bottom interior bevel 79 located on the interior portion of quad bottom 54 during ultrasonic welding of the quad upper housing 56 to quad bottom 54. This creates another positive seal as weld ring 55 creates extra plastic which during welding flows into empty cervices in the plastic to form a hermetic seal. Fourthly, side member 42 of quad bottom 54 is forcibility inserted into quad shear weld area 41 of quad upper housing 56. During assembly, pressure and heat from a bonding operation, such as ultrasonic welding, conjoins side member 42 into shear weld are 41 as there is an interference fit between side member 42 and shear weld area 41 such fit being defined by ultrasonic welding standards and the thermoplastic used in this apparatus. In the current invention, using ABS plastic, the interference is between 0.004 to 0.010 inch, preferably 0.007 inch. During ultrasonic welding or other conjoining activity, such as gluing, the thermoplastic will soften under pressure and will solidify upon the cooling of the plastic, creating another hermetic seal. Extra plastic that is expelled during the conjoining operation will gather in chamfer 57. Fifthly, top lip of solid enveloping member 73 is compacted against shelf 70 to further prevent the escapement of fluids. Circumferential side wall 72 of solid enveloping member 49 fits flush against without interference against quad upper housing side wall 71. These five methods of assuring complete containment of possible contaminated fluids allow for the manufacturing tolerances necessary for automated assembly.

Figure 7:
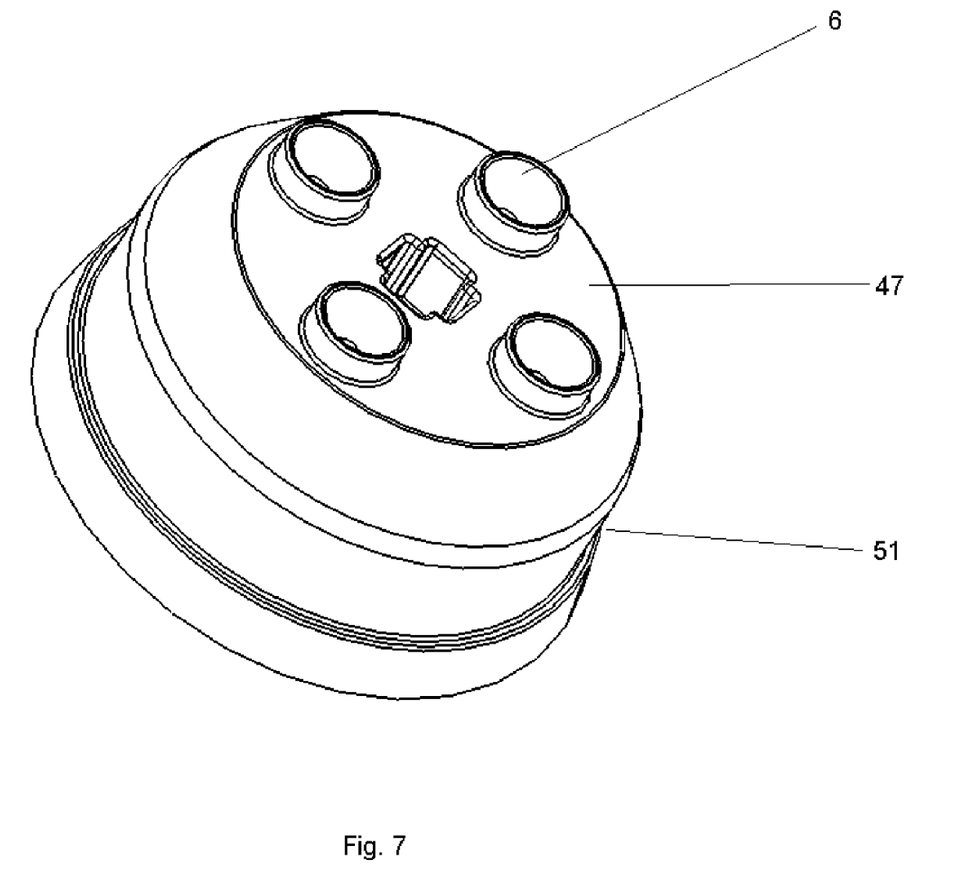
In FIG. 7, the 4 unit apparatus is shown assembled in a top view.
Figure 8:
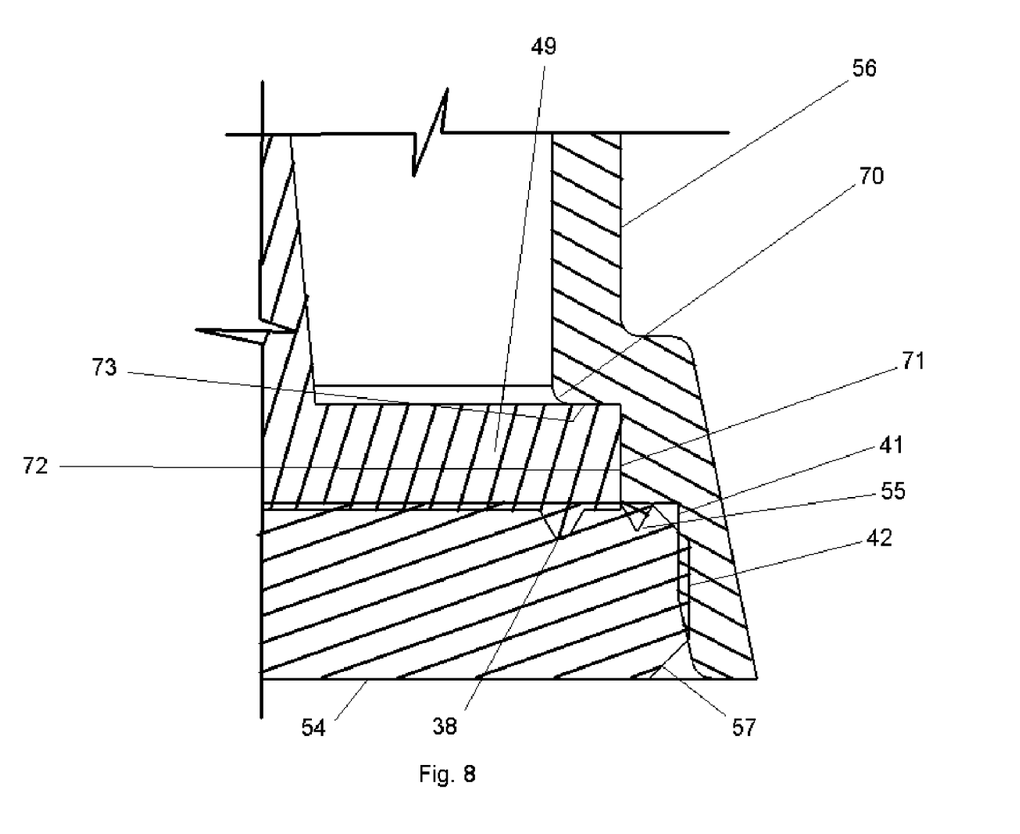
In FIG. 8, the drawing shows the joint area between the upper housing unit and the bottom lid in the 4 unit apparatus, detailing the duplicative seals points.

FIG. 7 shows an exterior top view of 4 unit apparatus 51. There are 4 targeting rings 6 that are located in a circular pattern along top of quad unit 47. Each targeting ring 6 is located at 90 degree intervals of along top of quad unit 47.

This invention is not limited to either a single or quad (4) unit apparatus. A 4 unit apparatus is shown as an example of the multiplicity of units that can be either linked together externally, as multiple apparatuses connected together, or units that may be linked internally in a single apparatus, as shown here as an example of 4 units in 1 apparatus. Any number of units are possible and other configurations other than circular are within the spirit and concept of this invention.

What is claimed is:

1. A medical sharps retardation apparatus for retarding the future use of medical sharps, such as a needle, said sharp having a hollow bore, circular in nature, having an exposed distal end capable of puncture or slicing and an enclosed proximal end opposed of said exposed end, each end located along a common axis and whereby said enclosed end is conjunctively attached to a medical apparatus which contains a reservoir which is fluidly connected to interior of said sharp, comprising;

an upper housing (2), having an exterior and interior, and an upper and lower portion, said upper portion being adapted for receiving said exposed end of said sharp allowing entrance into said interior of said apparatus through a centrally located passageway (14), said interior of said upper housing comprising gripping element alignment means (28), pivoting means (15), containment sealing means (61) hermetic sealing means and locating means (7), said locating means consisting of an inverse conically shaped ring designed to guide said sharp into said passageway;

an enveloping member (17) constructed of a material suitable for puncture by said sharp, said member located within, sharing a common longitudinal axis and in circumferential contact with said interior of said upper housing, said member configured with at least one buoying arm (19) and a bulbous hub, said arm concentrically located about said hub, said arm vertically emanating from an exterior side (25) of said member, upper circumferential ring (62) of said enveloping member being in compressive contact with said containment sealing means (61) of said upper housing, a set of gripping means (16) for facilitating uni-directional longitudinal access of said sharps through said centrally located passageway of said upper housing portion, said set held in vertical symmetry by said gripping element alignment means and having rotational contact with said pivoting means in said interior portion upper housing and in tangential contact with said buoying arm of said enveloping member, members of said set of said gripping means in circumferential contact with other member of said set, point of said circumferential contact located in longitudinal alignment with said centrally located passageway; and a bottom encasement lid adapted to seal hermetically with said interior of said upper housing, said hermetic seal being accomplished through a shear welding of vertically interfering walls (21, 59) and butt welding of horizontal surfaces (31, 60), said enveloping member hermetically sealing through compressive contact between lower side (64) of said enveloping member and an escapement prevention seal (18) of said lid.

2. A medical sharps retardation apparatus of claim 1, where said gripping means are 2 or more circular objects.

3. A medical sharps retardation apparatus of claim 1, where said gripping means are 2 or more cylindrical objects comprising of two flat sides and a circular perimeter located in between said flat sides.

4. A medical sharps retardation apparatus in claim 1 where said gripping means are made of a material that possesses a hardness higher than that of said sharp.

5. A medical sharps retardation apparatus in claim 4 where said gripping means are biased with a knurl pattern, said knurl pattern selected from at least one member of the group consisting of bi-directional knurl and uni-directional knurl.

6. A medical sharps retardation apparatus in claim 1 where said bulbous hub has a hollow interior, said hollow interior is conically shaped.

7. A medical sharps retardation apparatus in claim 1 where gripping means allow for passage of said sharp only in a single longitudinal direction concurrent with direction of said sharp subsequent to entry through said locating means, upon contact with gripping means, due to mechanical leverage.

8. A medical sharps retardation apparatus in claim 1 where said bulbous hub has a solid interior.

9. A medical sharps retardation apparatus in claim 1 where said gripping element alignment means are parallel structures whereby said gripping means are held between said parallel structures as to allow said gripping means to remain in tangential contact and are allowed unimpinged travel about said pivoting means.

10. A medical sharps retardation apparatus in claim 1 where said pivoting means allow for said gripping means to rotateably disengage tangential contact with the other said gripping means through an angle delta while maintaining tangential contact with said sharp.

11. A medical sharps retardation apparatus in claim 1 where said enveloping member is constructed of a polymer material with a high modulus of elasticity.

12. A medical sharps retardation apparatus in claim 1 where said upper housing portion and said bottom encasement lid are made of a thermoplastic polymer material.

13. A medical sharps retardation apparatus in claim 1, where said hermetic sealing means is region of bonding with said bottom encasement lid, constructed to maximize bonding adhesion, depending on type of bonding method.

14. A medical sharps retardation apparatus in claim 1 whereby said upper housing and said enveloping member are adapted to facilitate multiple said entrance points, each of said entrance points having a corresponding locating means, passageway, gripping element alignment means, pivoting means, and gripping means.

15. A medical sharps retardation apparatus in claim 1, where said medical apparatus is a hypodermic needle body.

16. A Method for retarding the future use of medical sharps and preventing contaminated fluid contained in and on said sharps escaping containment, such as a needle, said sharp having a hollow bore, circular in nature, having an exposed distal end capable of puncture or slicing and an enclosed proximal end opposed of said exposed end, each end located along a common axis and whereby said enclosed end is conjunctively attached to a medical fluids collection and delivery supply mechanism which contains a reservoir which is fluidly connected to interior of said sharp, steps comprising;
provoding an apparatus as in claim 1;
inserting sharp into said apparatus through a locating ring;
evacuating said reservoir of said contaminated fluid into said apparatus; and
deposing of said apparatus in an manner approved by governmental health control agencies.

17. The method in claim 16 whereby containment of bodily fluids on the exterior and interior of said sharp are contained inside of said apparatus.

18. The method in claim 16 whereby said sharp is permanently retarded from future use by restraint from inside of said apparatus.

19. The Method in claim 18 whereby said sharp is permanently retarded using mechanical leverage.

20. The method in claim 16 whereby multiple sharps are retarded from future use using a single apparatus with multiple locating rings.

21. A Method for retarding the future use of medical sharps and preventing contaminated fluid contained in and on said sharps escaping containment, such as a needle, said sharp having a hollow bore, circular in nature, having an exposed distal end capable of puncture or slicing and an enclosed proximal end opposed of said exposed end, each end located along a common axis and whereby said enclosed end is conjunctively attached to a medical fluids collection and delivery supply mechanism which contains a reservoir which is fluidly connected to interior of said sharp, steps comprising;
providing an apparatus as in claim 1;
inserting sharp into said apparatus;
evacuating said reservoir of said contaminated fluid into said apparatus;
removing said reservoir from said sharp; and
deposing of said apparatus in an manner approved by governmental health control agencies.

22. Method for retarding the future use of medical sharps and preventing contaminated fluid contained in and on said sharps escaping containment, such as a needle, said sharp having a hollow bore, circular in nature, having an exposed distal end capable of puncture or slicing and an enclosed proximal end opposed of said exposed end, each end located along a common axis and whereby said enclosed end is conjunctively attached to a medical fluids collection and delivery supply mechanism which contains a reservoir which is fluidly connected to interior of said sharp, steps comprising;
providing an apparatus as in claim 1 having a transparent bottom encasement lid;
inserting sharp into said apparatus;
evacuating said reservoir of said contaminated fluid into said apparatus;
visually confirming evacuation of elements from said sharp by observing the presence or absence of fluids being evacuated;
removing said reservoir from said sharp; and
deposing of said apparatus in an manner approved by governmental health control agencies.

* * * * *